US010772667B2

(12) United States Patent
Ramsay et al.

(10) Patent No.: US 10,772,667 B2
(45) Date of Patent: Sep. 15, 2020

(54) BONE SCREW WITH CUTTING TIP

(71) Applicant: Medos International Sarl, Le Locle (CH)

(72) Inventors: Chris Ramsay, West Wareham, MA (US); Joseph Peterson, South Dartmouth, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 92 days.

(21) Appl. No.: 15/852,310

(22) Filed: Dec. 22, 2017

(65) Prior Publication Data

US 2019/0192203 A1 Jun. 27, 2019

(51) Int. Cl.
*A61B 17/86* (2006.01)
*A61B 17/70* (2006.01)
*A61B 17/16* (2006.01)
*A61B 90/00* (2016.01)

(52) U.S. Cl.
CPC ...... *A61B 17/8625* (2013.01); *A61B 17/7035* (2013.01); *A61B 17/7085* (2013.01); *A61B 17/863* (2013.01); *A61B 17/864* (2013.01); *A61B 17/8605* (2013.01); *A61B 17/8635* (2013.01); *A61B 17/1671* (2013.01); *A61B 17/8685* (2013.01); *A61B 2090/037* (2016.02)

(58) Field of Classification Search
CPC .... A61B 17/863; A61B 17/8635; A61B 17/86
USPC .................................................. 606/301–321
See application file for complete search history.

(56) References Cited

U.S. PATENT DOCUMENTS

| 5,300,076 | A | | 4/1994 | Leriche |
| 5,364,400 | A | * | 11/1994 | Rego, Jr. ............ A61B 17/8645 606/304 |
| 5,443,509 | A | * | 8/1995 | Boucher .............. A61B 17/861 411/412 |
| 5,593,410 | A | | 1/1997 | Vrespa |
| 5,733,307 | A | | 3/1998 | Dinsdale |
| 5,928,236 | A | | 7/1999 | Augagneur et al. |
| 5,968,078 | A | | 10/1999 | Grotz |
| 6,306,140 | B1 | | 10/2001 | Siddiqui |
| 6,398,785 | B2 | | 6/2002 | Carchidi et al. |
| 6,517,542 | B1 | | 2/2003 | Papay et al. |
| 6,736,820 | B2 | | 5/2004 | Biedermann et al. |

(Continued)

FOREIGN PATENT DOCUMENTS

| FR | 2932975 A1 | 1/2010 |
| FR | 2971413 A1 | 8/2012 |

(Continued)

OTHER PUBLICATIONS

"International Search Report and Written Opinion received for PCT Patent International Application No. PCT/US2018/065966", dated Apr. 12, 2019, 20 pages.

*Primary Examiner* — Matthew J Lawson
(74) *Attorney, Agent, or Firm* — Mintz Levin Cohn Ferris Glovsky and Popeo, P.C.

(57) ABSTRACT

Various bone screws configured to be implanted into bone and methods of use are provided. In an exemplary embodiment, a bone screw is provided with an elongate shank having at least two threads thereon, and having a distal facing surface with at least two cutting edges. The cutting edges can be configured to cut bone as the bone screw is rotated into bone, thereby forming a path for the threads.

14 Claims, 12 Drawing Sheets

(56) References Cited

U.S. PATENT DOCUMENTS

| | | |
|---|---|---|
| 6,743,233 B1 | 6/2004 | Baldwin et al. |
| 6,755,835 B2 | 6/2004 | Schultheiss et al. |
| 6,974,460 B2 | 12/2005 | Carbone et al. |
| 7,008,227 B2 | 3/2006 | Carmichael et al. |
| 7,179,261 B2 | 2/2007 | Sicvol et al. |
| 7,198,488 B2 | 4/2007 | Lang et al. |
| 7,819,905 B2 | 10/2010 | Newcomb et al. |
| 8,029,285 B2 | 10/2011 | Holmen et al. |
| 8,333,590 B2 | 12/2012 | Hansson |
| 8,414,628 B2 | 4/2013 | Melkent |
| 8,945,190 B2 | 2/2015 | Culbert et al. |
| 9,079,263 B2 | 7/2015 | Reed |
| 9,168,077 B2 | 10/2015 | Whitmore |
| 9,358,057 B1 | 6/2016 | Whipple et al. |
| 9,848,962 B2* | 12/2017 | Moon ............... A61C 8/0089 |
| 10,092,341 B2* | 10/2018 | Ellis ............... A61B 17/8635 |
| 2003/0069582 A1 | 4/2003 | Culbert |
| 2004/0044345 A1 | 3/2004 | DeMoss et al. |
| 2004/0106925 A1* | 6/2004 | Culbert ............ A61B 17/0401 |
| | | 606/312 |
| 2005/0021036 A1 | 1/2005 | Whitmore et al. |
| 2005/0101961 A1 | 5/2005 | Huebner et al. |
| 2006/0100627 A1* | 5/2006 | Stone ............... A61B 17/0642 |
| | | 424/426 |
| 2006/0217727 A1* | 9/2006 | Munro ............... A61B 17/74 |
| | | 606/312 |
| 2007/0162028 A1 | 7/2007 | Jackson et al. |
| 2007/0162029 A1 | 7/2007 | Whitmore |
| 2010/0114174 A1 | 5/2010 | Jones et al. |
| 2010/0211118 A1 | 8/2010 | Christen et al. |
| 2011/0070558 A1* | 3/2011 | Park ............... A61B 17/863 |
| | | 433/174 |
| 2011/0288599 A1 | 11/2011 | Michielli et al. |
| 2011/0295319 A1 | 12/2011 | Duplessis et al. |
| 2012/0203290 A1 | 8/2012 | Warren et al. |
| 2013/0053901 A1 | 2/2013 | Cormier et al. |
| 2013/0096618 A1 | 4/2013 | Chandanson et al. |
| 2014/0058460 A1 | 2/2014 | Reed |
| 2014/0081339 A1* | 3/2014 | Bowman ............. A61F 2/0811 |
| | | 606/304 |
| 2014/0114312 A1 | 4/2014 | Krause |
| 2014/0234800 A1 | 8/2014 | Laster |
| 2014/0257409 A1 | 9/2014 | Reed |
| 2014/0277188 A1* | 9/2014 | Poulos ............. A61B 17/1655 |
| | | 606/304 |
| 2014/0303676 A1* | 10/2014 | Stroncek ........... A61B 17/8645 |
| | | 606/304 |
| 2015/0044639 A1 | 2/2015 | Carlsson et al. |
| 2015/0196388 A1* | 7/2015 | Housman ........... A61B 17/0401 |
| | | 606/304 |
| 2015/0230844 A1* | 8/2015 | Ellis ............... A61B 17/8635 |
| | | 606/316 |
| 2016/0081771 A1 | 3/2016 | Fromovich et al. |
| 2016/0113693 A1 | 4/2016 | Denis et al. |
| 2019/0223917 A1* | 7/2019 | Gray ............... A61B 17/7037 |

FOREIGN PATENT DOCUMENTS

| | | |
|---|---|---|
| FR | 3000662 A3 | 7/2014 |
| FR | 3000664 A3 | 7/2014 |
| FR | 3021206 A1 | 11/2015 |
| WO | 2015091916 A1 | 6/2015 |

* cited by examiner

BONE SCREW WITH CUTTING TIP

FIELD

Bone screws having an improved cutting tip, and methods for using the same, are provided herein.

BACKGROUND

A variety of conditions can result in the need for manipulation or treatment of spinal conditions, and many spinal procedures require the use of one or more bone screws. In particular, bone screws can be used in the spine to correct deformities and treat trauma and/or degenerative pathologies. For example, bone screws can be used in instrumentation procedures to affix rods and/or plates to the spine, can be used to immobilize part of the spine to assist fusion by holding bony structures together, and can be used in a variety of other operations to treat spinal conditions. Bone screws can provide a means of anchoring or securing various elements to a spinal segment during these procedures.

In such operations, it is important to accurately insert bone screws at an entry point of choice. It is also important to reduce the tendency of bone screws to turn or skive out of the entry point during the initial insertion attempt. Another desirable attribute would be reducing the number of instruments needed to prepare the boney anatomy for insertion. Initial screw insertion can be a significant challenge, adding difficulty and danger to an operation while possibly requiring additional equipment to prepare an entry point for correct screw placement. One approach to reduce the need for additional equipment is to create a flute, or a vertical cut or groove, in the thread of the screw. This flute feature forms a vertical edge to cut bone as the screw is rotated into bone. However, this approach results in reduced fixation within the boney anatomy once the screw is completely inserted. This reduced fixation potential is amplified with shorter screws.

Accordingly, there remains a need for bone screws having an improved structure for initial screw insertion that reduces the need for additional instruments to prepare an entry point and does not sacrifice potential screw fixation, especially in shorter screw lengths.

SUMMARY

Bone screws and methods for making and using a bone screw are provided herein. In one embodiment, a bone screw is provided that includes an elongate shank defining a central longitudinal axis and having a proximal end, a distal end with a conical distal tip region that tapers distally inward, and a distal facing surface. The bone screw also includes at least two threads formed on the elongate shank. Each thread can terminate at the distal end in a leading cutting edge positioned radially outward of the central longitudinal axis and defined by an intersection between a proximal-facing surface of the thread and the distal facing surface of the conical distal tip region.

The bone screw can have a variety of configurations. For example, the bone screw can have first and second threads that are offset from one another by 180 degrees. In other aspects, the at least two threads can be radially equidistant from each other around the elongate shank.

In other embodiments, the distal facing surface can have an oblong shape with first and second curved edges extending along opposed sides thereof. The first and second curved edges can each have a concave region and a convex region. The leading cutting edge of each of the at least two threads can extend along the concave region. In other aspects, the first and second curved edges can each have a concave region and a convex region, and the convex regions can be positioned circumferentially about the central longitudinal axis.

In another embodiment, the bone screw can include a distal protrusion extending distally from the distal facing surface along the central longitudinal axis. The distal protrusion can have a diameter that is less than a minor diameter of the elongate shank.

In other aspects, the distal facing surface can have a conical shape and can form an acute angle with a plane extending perpendicular to the central longitudinal axis of the elongate shank. In other embodiments, the distal facing surface can extend proximally from the at least two cutting edges such that the distal facing surface is concave.

In another embodiment, a bone screw is provided and has an elongate shank with a proximal end, a distal end, and a central longitudinal axis extending therebetween. The elongate shank can have a major diameter along at least a proximal portion thereof, a conical distal tip region at the distal end that tapers distally inward, and a distal facing surface having an edge defining an outer perimeter of the distal facing surface. The bone screw can also include at least two cutting edges formed along a portion of the outer perimeter of the distal facing surface, and at least two threads extending along the elongate shank. Each thread can have a proximal surface and a distal surface, and the proximal surface of each thread can terminate at one of the at least two cutting edges.

The bone screw can have a variety of configurations. For example, the distal facing surface of the elongate shank can be concave. In certain embodiments, the at least two cutting edges can be positioned distally of a mid-point of the distal facing surface positioned on the central longitudinal axis. In other embodiments, the bone screw can include first and second threads that are offset from one another by 180 degrees.

In other embodiments, at least a portion of the edge defining the outer perimeter of the distal facing surface can be defined by an intersection between the distal facing surface and the distal surface of the at least two threads. In other aspects, the outer perimeter of the distal facing surface can have an oblong shape with concave regions and convex regions.

The bone screw can include other features, such as a distal protrusion extending distally from the distal facing surface along the central longitudinal axis, the distal protrusion having a diameter that is less than a minor diameter of the elongate shank.

Methods for implanting a bone screw in the cervical spine are also provided. In one embodiment, the method can include positioning at least two cutting edges formed along an outer perimeter of a distal facing surface of a bone screw in contact with a bone surface in the cervical spine of a patient. The at least two cutting edges can thus engage the bone surface. The at least two cutting edges can be defined by a portion of the outer perimeter of the distal facing surface and a proximal surface of at least two threads extending along the bone screw. The method can further include rotating the bone screw such that the at least two cutting edges threads cut away bone to advance the bone screw into bone.

In one embodiment, the bone screw can be positioned at an angle other than 90 degrees relative to the bone surface. In other aspects, positioning the at least two cutting edges in contact with the bone can include inserting a distal protrusion on the distal facing surface into a guide hole formed in the bone.

In another embodiment, a central region of the distal facing surface can be positioned proximal of the at least two cutting edges such that the central region does not contact the bone surface when the at least two cutting edges are positioned in contact with the bone surface.

BRIEF DESCRIPTION OF THE DRAWINGS

The invention will be more fully understood from the following detailed description taken in conjunction with the accompanying drawings, in which.

DETAILED DESCRIPTION

Figure 1A:
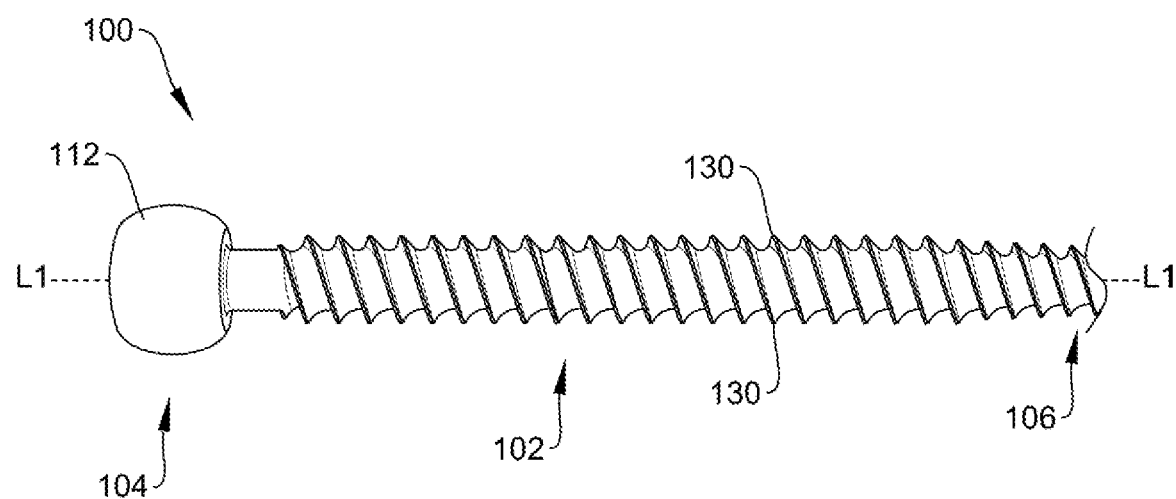
FIG. 1A is a side view of one embodiment of a bone screw.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

When advancing bone screws into bone, particularly in the cervical spine, surgeons are often required to advance the screws at a variety of angles and from a variety of positions. These varying advancement conditions can make successfully advancing the screw a challenge. Thus various screws are provided herein that are configured to be implanted in bone, such as in the cervical spine, that can be advanced at a variety of angles with or without a guide hole in the bone. While the bone screws are described in connection with spinal operations and particularly placement in the cervical spine, the screws can be used in connection with any type of bone, tissue (such as in a suture anchor or for lagging soft tissue to bone such as in a shoulder), or in other non-surgical applications.

In an exemplary embodiment, a bone screw is provided with an elongate shank having a distal end or tip that is configured to cut bone as the bone screw is threaded into bone. The screw can have at least two threads extending along the elongate shank. The distal tip portion of the bone screw can have a distal facing surface, and each of the threads and the distal facing surface can define cutting edges that are positioned radially outward from a central longitudinal axis of the elongate shank. The cutting edges can be distal of at least a portion of the distal facing surface to allow the cutting edges to contact bone upon placement of the screw against bone at a variety of angles relative to the surface of bone. As a result, when the screw is rotated, the cutting edges can be configured to engage and cut into bone, allowing the screw to create its own path into bone.

FIGS. 1A-1I illustrate one embodiment of a bone screw 100 with an elongate shank 102 having a proximal end 104, a distal end 106, and a central longitudinal axis L1. The screw 100 can include a head 112 at the proximal end having a drive feature 114 configured to couple with a driver tool (not shown) for advancing the screw 100 into bone. The screw can also have two or more threads formed therealong that terminate at a distal tip on the distal end 106 that is configured to cut bone.

Figure 1B:
FIG. 1B is a side view of the shank of the bone screw of FIG. 1A, with the threads removed.
Figure 1C:
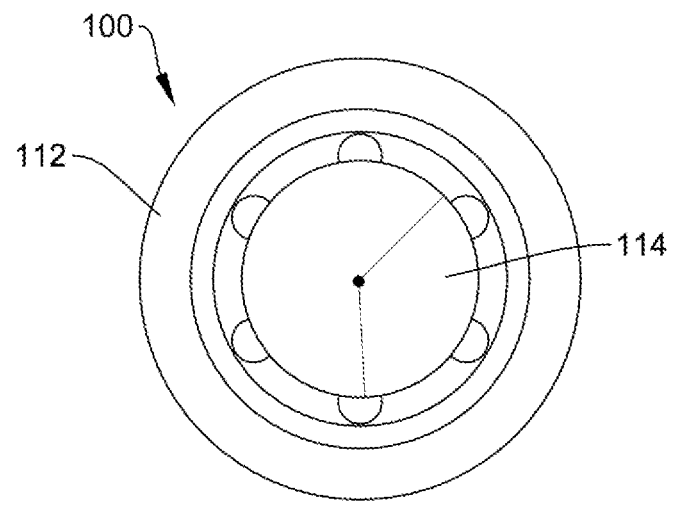
FIG. 1C is a proximal-to-distal end view of the bone screw of FIG. 1A.

The head 112 of the bone screw 100 can have various configurations, and various drive features can be formed in or on the head. As illustrated in FIG. 1C, the drive feature 114 can be configured to receive a driver tool, such as a screw driver, a hexagonal driver, etc. Any complementary mating features can be used, however. In other embodiments, the head can be shaped to be received in a drive socket of a driver tool, or alternatively the bone screw can be headless, and the shank can mate with a driver tool (not shown).

The elongate shank 102 of the bone screw 100 can also have various configurations. The elongate shank 102 is shown in FIG. 1B with the threads removed. As shown, the illustrated shank 102 has a cylindrical body with a constant diameter extending along a majority thereof, representing a minor diameter of the bone screw 100. The shank can be tapered distally, for example at the distal end, transitioning from a larger diameter to a smaller distal-most diameter. For example, the diameter can be constant along approximately 70 to 85% of the total length of the shank 102, with the tapered distal end being 15 to 30%. In other embodiments, the shank 102 can taper along the entire length with a larger diameter at a proximal end of the shank tapering to a smaller diameter at a distal end thereof. Accordingly, tapering of the shank can be continuous along the length of the shank such that the diameter decreases at a constant rate along the length thereof, or tapering can be located just at a distal end thereof such that only a distal portion of the shank is tapered while a proximal portion has a constant diameter.

As indicated above, the elongate shank can include threads formed therealong. In the illustrated embodiment, the screw 100 has two threads 130 formed on an external surface thereof, but two or more threads can be used, for example two, three, four, or five threads. In the illustrated embodiment, the threads 130 start on opposite sides (e.g., 180 degrees apart) of the shank 102 so that they are opposed to each other and extend in a rotating pattern along at least part of the elongate shank 102 between the proximal end 104 and the distal end 106 to form a helix. Regardless of the number of threads formed therealong, the threads are preferably positioned equidistant from each other around the shank 102 such that the thread starts are balanced with each other. The threads 130 can each have a distal-most end that terminates at or near a cutting edge 122, as discussed in further detail below. The threads 130 can have an approximately constant thread pitch as well as a constant lead along the entire length of the shank 102.

Figure 1D:
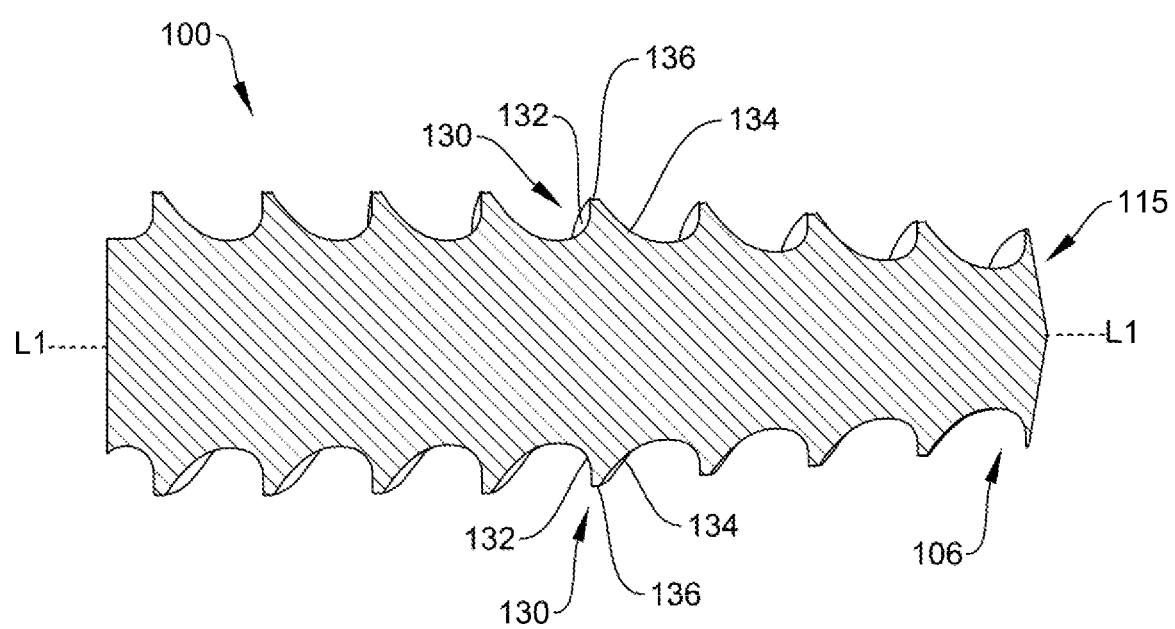
FIG. 1D is a cross-sectional side view of a distal portion of the bone screw of FIG. 1A.
Figure 1E:
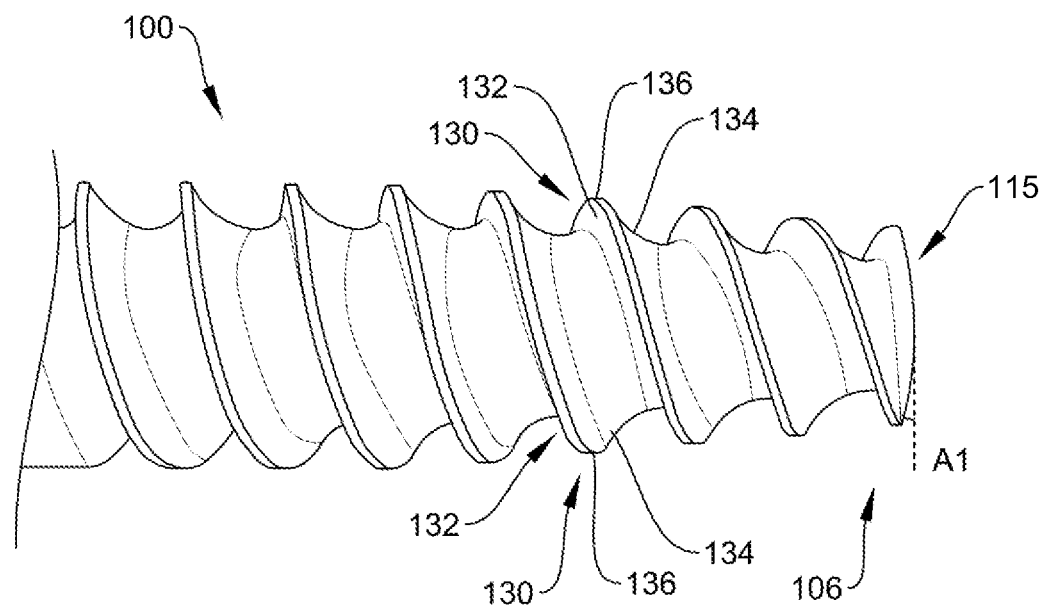
FIG. 1E is a side view of a distal portion of the bone screw of FIG. 1A.

In the illustrated embodiment, each of the threads 130 has a proximal surface 132 that faces proximally, a distal surface 134 that faces distally, and an outer-most radial surface 136 that can extend at an angle between and relative to the proximal and distal facing surfaces 132, 134. A thread profile of each of the threads 130 can be, for example, square or rectangular in shape. In other embodiments, the thread profile of the threads can be triangular with no radial surface, rounded, etc., and a height and a width of each of the threads can vary. In the illustrated embodiment, the threads are not symmetrical, such that the proximal surface 132 extends to the outer-most radial surface 136 at a steeper angle relative to a plane perpendicular to the longitudinal axis L1 as compared to the distal surface 134, as seen in FIGS. 1D and 1E. However, symmetrical threads can be used in various embodiments.

Other exemplary thread forms are disclosed, for example, in U.S. Patent Application Publication No. 2011/0288599, filed on May 18, 2011, and in U.S. Patent Application Publication No. 2013/0053901, filed on Aug. 22, 2012, both of which are hereby incorporated by reference herein in their entireties.

The threads discussed herein, including the number of threads, the pitch, the lead, major and minor diameters, and thread shape, can be selected to facilitate engagement with bone. Additionally, the diameters of the threads can vary similar to the diameter of the elongate shank discussed above, wherein diameters of the thread(s) represent major diameters of the bone screws. As discussed above with the diameter of the elongate shank representing a minor diameter, the major and minor diameters of a bone screw can taper from one end to the other of a bone screw, such as from a proximal end to a distal end. The major and minor diameter taper can be the same or different. The start of the major and minor diameter taper can be at the same location along an elongate shank of a bone screw or can be different, resulting in constant crest width or varying crest width. The major diameter can represent the largest diameter of a screw thread, whereas the minor diameter can represent the smallest diameter of a screw thread. While threads are shown herein, other surface features can be used in other embodiments. For example, in some embodiments, bone screws can be configured to permit the screw to rotate in one direction but resist or prevent rotation in the opposite direction and/or can include cleats, spikes, friction-fit features, etc., formed thereon.

Figure 1F:
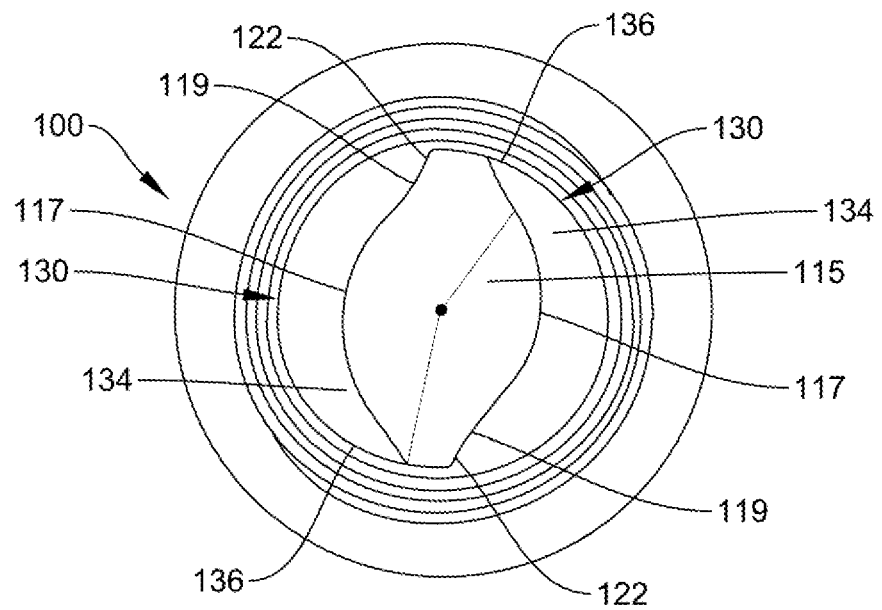
FIG. 1F is a distal-to-proximal end view of the bone screw of FIG. 1A.

The screw 100 can also have a variety of different distal tip configurations. For example, as illustrated in FIGS. 1F-1I, the distal end 106 of the bone screw 100 can have a distal facing surface 115 that forms the distal-most surface of the bone screw 100. As best shown in FIGS. 1F and 1H, the distal facing surface 115 can have an outer edge extending therearound and defining a perimeter of the distal facing surface 115. While the shape of the distal facing surface 115 can vary, in the illustrated embodiment, the distal facing surface 115 is substantially oblong, with concave and convex regions formed along the outer edge defining the perimeter. In an exemplary embodiment, the distal facing surface 115 has opposed convex regions 117 that are positioned radially about the central longitudinal axis and that define the majority of the outer perimeter. Smaller opposed concave regions 119 extend along opposed ends of the distal facing surface 115 and are spaced further radially outward of the convex regions 117.

The shape of the distal facing surface 115 can vary, but in the illustrated embodiment it has a slight tip or point formed at the mid-point thereof, aligned with the central longitudinal axis L1. This can result in a slight conical shape of the distal facing surface 115, for example as illustrated in FIG. 1D, such that when viewed along a cross-section extending through the axis L1, the distal end 106 of the screw 100 can be convex. The distal facing surface 115 of the screw 100 can thus define an acute angle Al with a plane extending perpendicular to the central longitudinal axis L1 and extending through the mid-point at the distalmost point. In certain exemplary embodiment, the angle Al can be, for example, about 10 degrees. This conical shape can facilitate effective docking of the bone screw 100 in bone while still allowing the cutting edges 122 to directly engage bone.

Figure 1G:
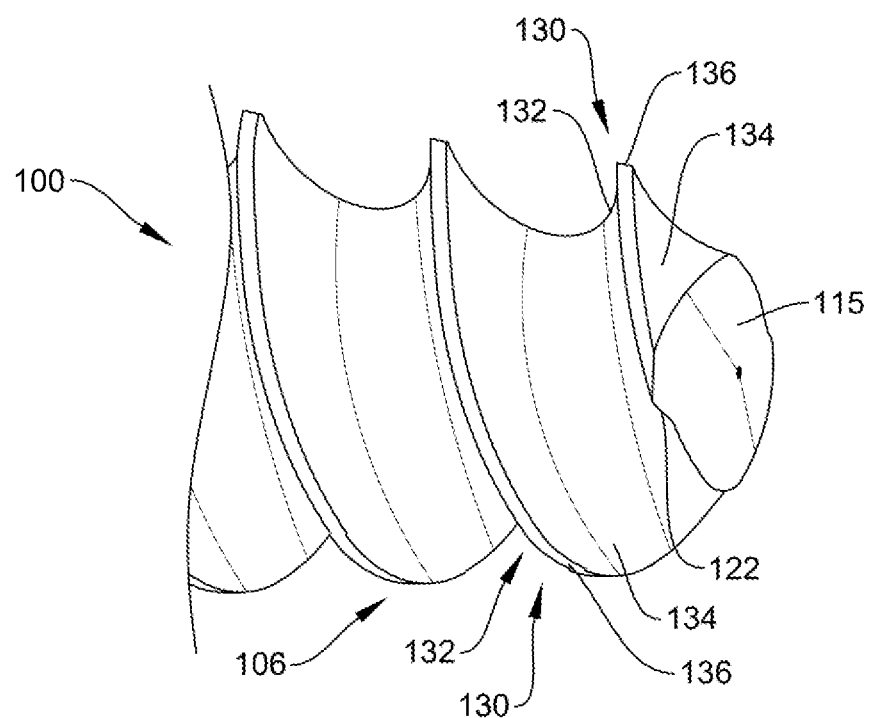
FIG. 1G is a perspective view of the distal tip of the bone screw of FIG. 1A.
Figure 1H:
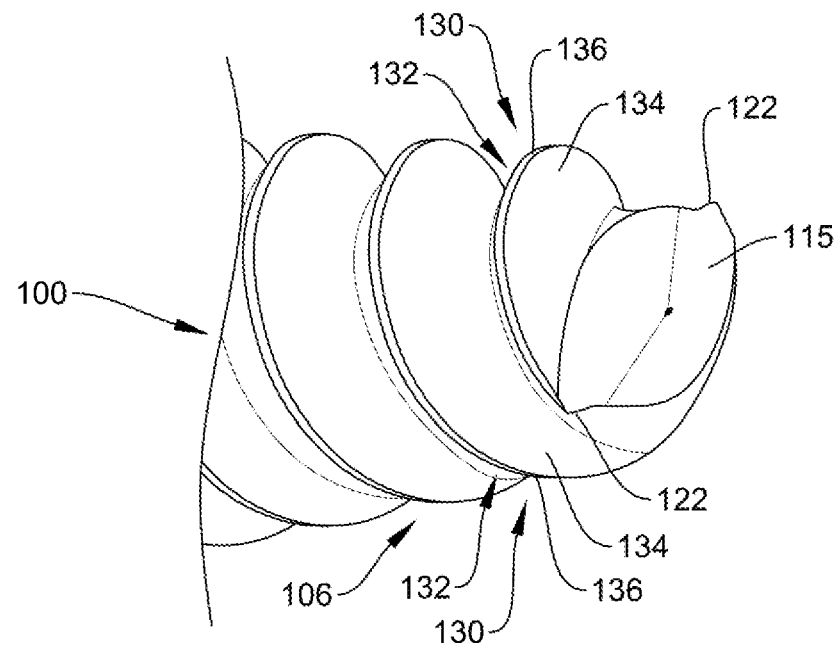
FIG. 1H is another perspective view of the distal tip of the bone screw of FIG. 1A.
Figure 1I:
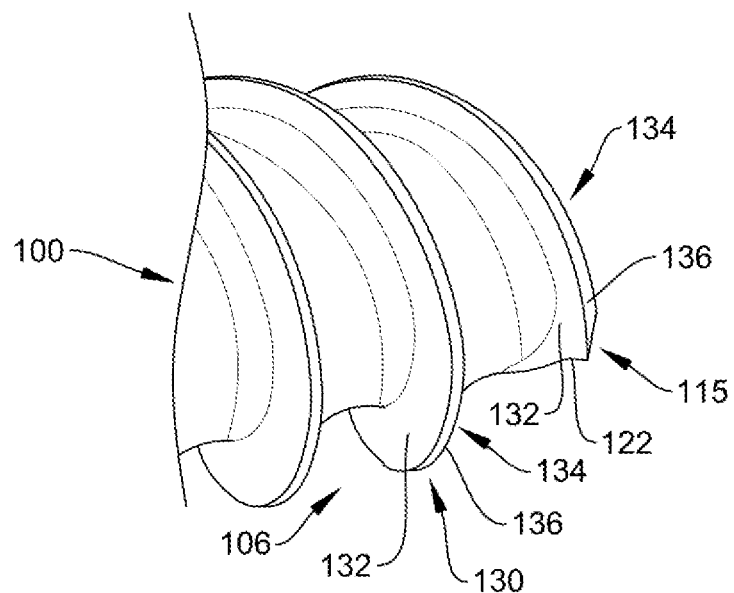
FIG. 1I is another perspective view of the distal tip of the bone screw of FIG. 1A.

As illustrated in FIGS. 1F-1I, the distal end 106 can also have the two or more cutting edges 122 formed thereon that are configured to facilitate cutting of bone during rotation of the bone screw 100 into bone. The cutting edges 122 can be formed along a portion of the outer perimeter of the distal facing surface 115. In the illustrated embodiment, the cutting edges 122 are formed along the concave regions 119 of the perimeter of the distal facing surface 115, and on opposed sides of the bone screw at a location radially outward of the central longitudinal axis Al. The cutting edges 122 can be defined by an intersection of the distal facing surface 115 and the proximal surface 132 of each thread 130. The distal surface 134 of each thread can terminate prior to the cutting edge 122, as best shown in FIG. 1G. In particular, in the illustrated embodiment, the proximal surface 134 and the outer-most radial surface 136 of each thread taper toward one another at the distal terminal end of the thread, terminating at one end of the cutting edge 122. As a result of this configuration, the distal surface 134 of each thread at the distal end of the bone screw extends between the outer-most radial surface 136 of the thread and the distal facing surface 115 of the bone screw.

Continuing to refer to FIGS. 1F-1I, and as indicated above, each cutting edge 122 can have a concave curved shape, defining a portion of the outer perimeter of the distal facing surface 115. While curved, the cutting edges 122 can generally extend radially between the longitudinal axis L1 and the outer diameter of the bone screw 100. As a result of the shape and position of the cutting edges 122, the cutting edges 122 are configured to cut bone as the screw is rotated into bone, thereby forming a path for the threads. Effective engagement and cutting can also be achieved even at extreme non-perpendicular angles relative to a bone surface, which are often required in the cervical spine. For example, a user can advance the screw 100 into bone even when the screw 100 is at an oblique or acute angle relative to the surface of bone, such as about 18 to 20 degrees. The distal end or tip of the bone screw 100, including the cutting edges 122, can thus be configured to maximize the efficiency of the bone screw 100 and to minimize the torque and downward force required to drive the bone screw 100 into bone.

Figure 2:
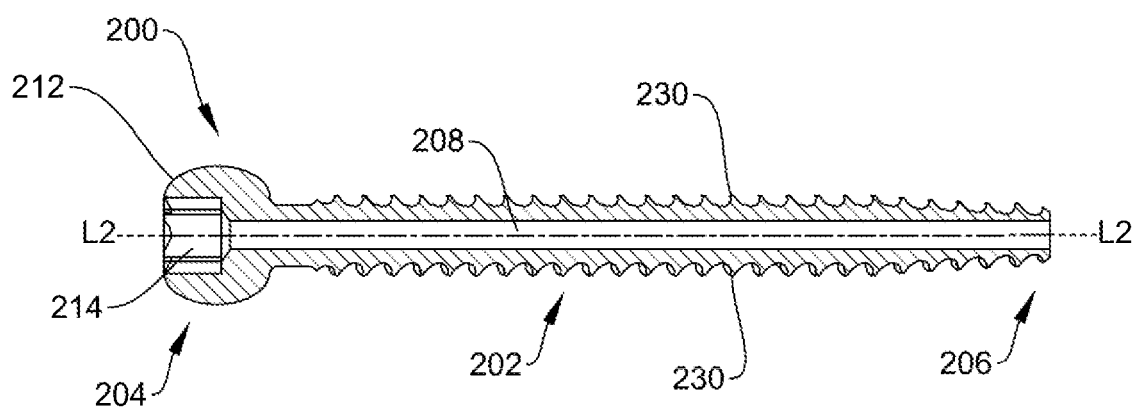
FIG. 2 is a cross-sectional side view of another embodiment of a bone screw.

While bone screw 100 does not have any inner lumen or cannulation, an inner lumen may be provided for certain applications, as may be desired. For example, FIG. 2 illustrates a bone screw 200 similar to bone screw 100 with an elongate shank 202 having a proximal end 204, a distal end 206, and a longitudinal axis L2. The illustrated screw 200 also includes a head 212 having a drive feature 214 configured to couple with a driver tool (not shown) for advancing the screw 200 into bone. The screw can have two or more threads 230 formed therealong that terminate at a distal tip on the distal end 106 with leading cutting edges that are configured to cut bone. An inner lumen 208 is shown extending entirely therethrough along the axis L2, and the inner lumen 208 can be configured to receive a guidewire for facilitating placement of the bone screw in bone and/or bone cement to assist in anchoring the bone screw.

Additionally, the distal end of the bone screw can be altered to bring the cutting edges of the bone screw into even greater engagement with bone. For example, a concave distal facing surface can be used to allow the cutting edges to have greater direct and immediate engagement with bone when advancing a screw into bone. As illustrated in FIGS. 3A-3E, a bone screw 300, similar to bone screw 100, can have an elongate shank 302 having a proximal end 304 and a distal end 306. The screw 300 can include a head 312 with a drive feature 314 configured to couple with a driver tool (not shown) for advancing the screw 300 into bone. The screw can have two or more threads 330 formed therealong. Each of the threads 330 can have a proximal surface 332 that faces proximally, a distal surface 334 that faces distally, and an outer-most radial surface 336 that can extend between and at an angle to the proximal and distal facing surfaces 332, 334. The threads 330 can terminate at a distal tip on the distal end 306 with leading cutting edges 322 that are configured to cut bone, similar to the cutting edges 122 discussed above.

Figure 3A:
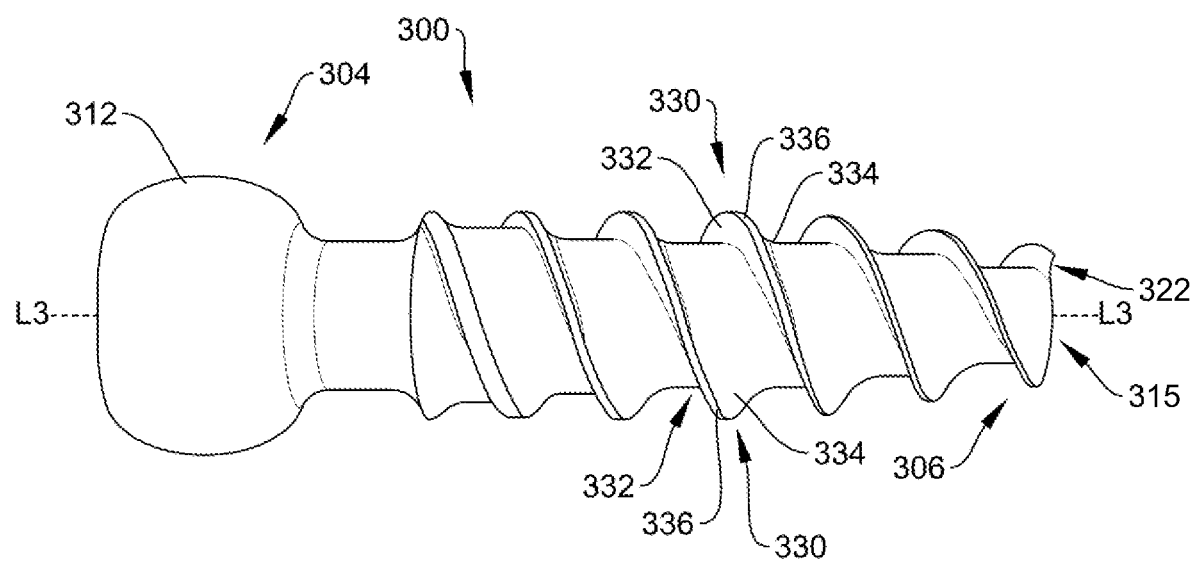
FIG. 3A is a side view of another embodiment of a bone screw.
Figure 3B:
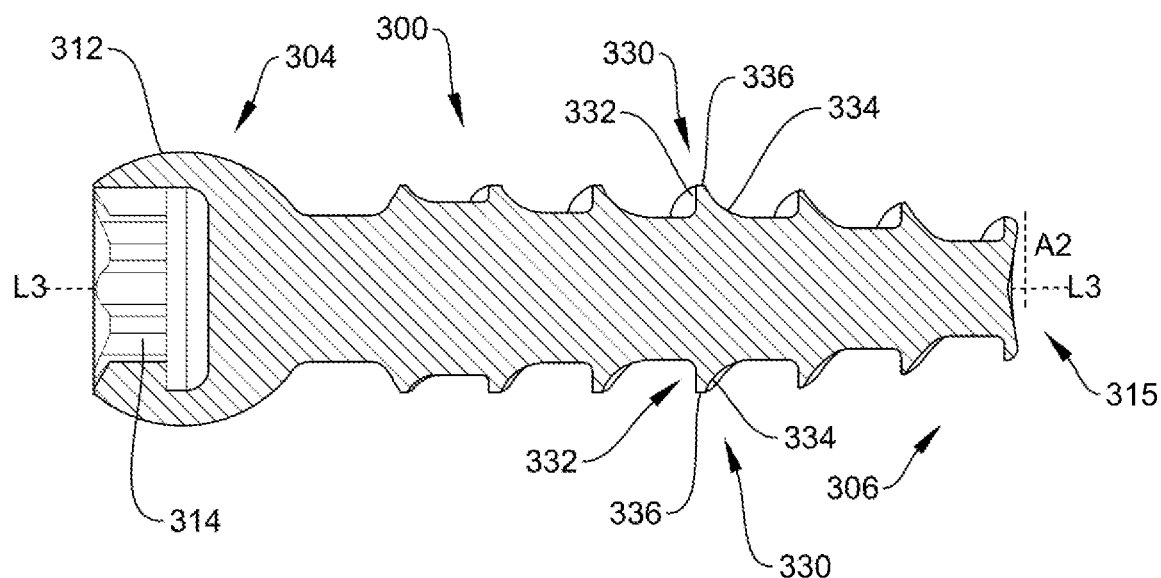
FIG. 3B is a cross-sectional side view of the bone screw of FIG. 3A.

In this embodiment, the distal facing surface 315 is concave, with the mid-portion being positioned more proximal than the outer edges of the distal facing surface 315. When viewed along a longitudinal cross-section as shown in FIG. 3B, the distal end 306 of the screw 300 can have a bowl shape such that the bone screw is configured to allow direct and unobstructed contact between the cutting edges 322 and bone when the screw 300 is advanced into bone. In other words, the cutting edges 322 are more distal then the mid-portion of the distal facing surface 315. The distal facing surface 315 can thus have sidewalls that extend at an acute angle relative to a plane extending perpendicular to the longitudinal axis L3. In certain exemplary embodiments, the angle can be about −10 degrees.

Figure 3C:
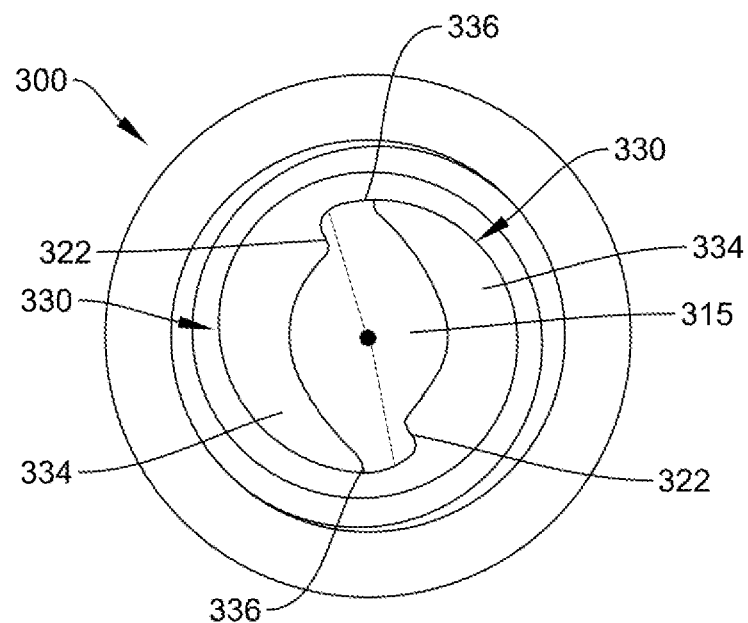
FIG. 3C is a distal-to-proximal end view of the bone screw of FIG. 3A.
Figure 3D:
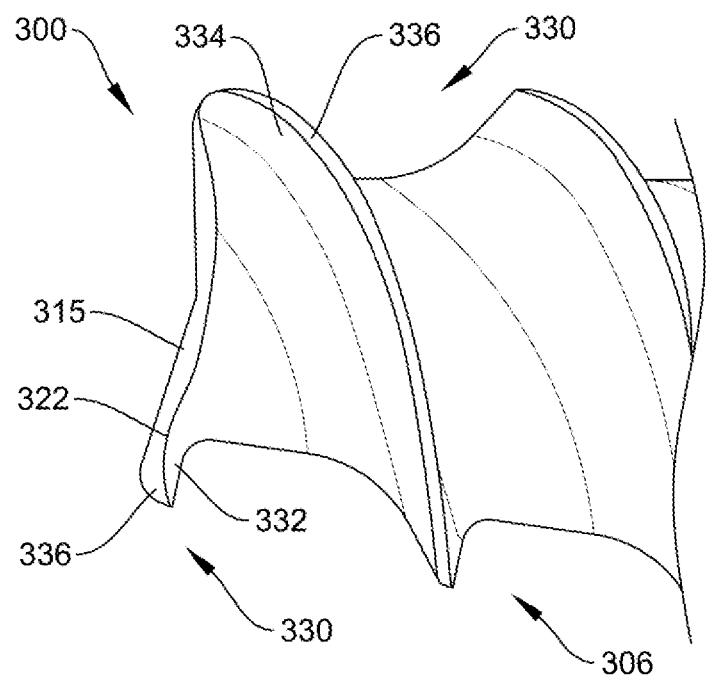
FIG. 3D is a perspective view of a cross-sectional portion of the distal tip of the bone screw of FIG. 3A.
Figure 3E:
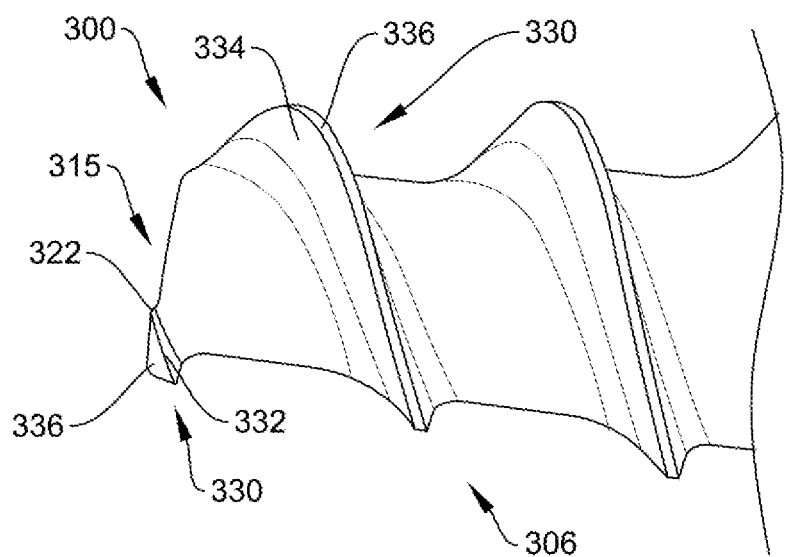
FIG. 3E is another perspective view of the cross-sectional portion of the distal tip of the bone screw of FIG. 3D.

Similar to the prior embodiment, and as illustrated in FIGS. 3C-3E, the cutting edges 322 can be formed along an outer perimeter of the distal facing surface 315 on opposed sides thereof. Each cutting edges 322 can be defined by an intersection between the distal facing surface 315 and the proximal surface 332 of each of the threads 330, similar to cutting edges 122. The cutting edges 322 can extend radially outward between a longitudinal axis L3 of the bone screw 300 and an outer diameter of the bone screw 300. Each cutting edge 322 can also have a curved concave shape. The outer perimeter of the distal facing surface 315 can also include convex regions, similar to those discussed above with respect to surface 115. In use, because the distal facing surface 315 is concave, the cutting edges 322 protrude distally into even greater engagement with bone, without any point of contact on the distal end 306 of the screw 300 until the cutting edges 322 engage bone. The cutting edges 322 can thus effectively cut bone from a variety of different angles, allowing a user to place the screw 300 into bone in numerous different operational situations while allowing the screw 300 to create its own path into bone. For example, a user can advance the screw 300 into bone even when the screw 300 is at an oblique or acute angle relative to the surface of bone, such as about 18 to 20 degrees. The cutting edges 322 can be configured to maximize the efficiency of the bone screw 300 and to minimize the torque and downward force required to drive the bone screw 300 into bone while also removing any distal protrusion that can accidentally interfere with operation of the cutting edges 322.

Figure 4:
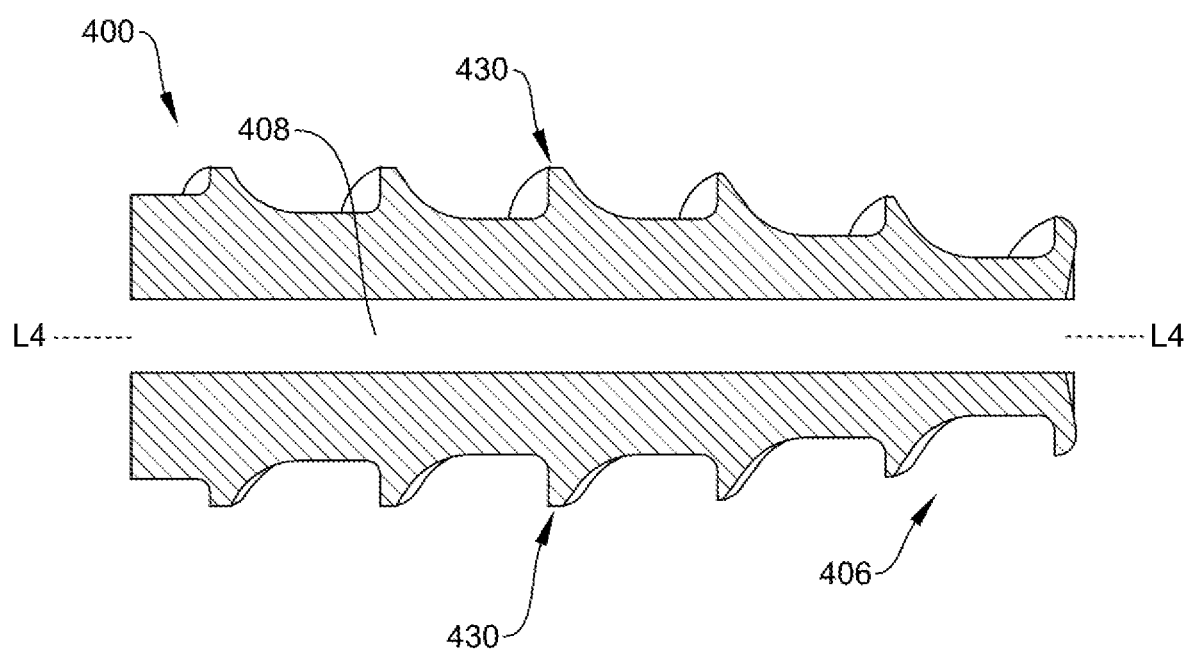
FIG. 4 is a cross-sectional side view of a distal tip of another embodiment of a bone screw.
Figure 5A:
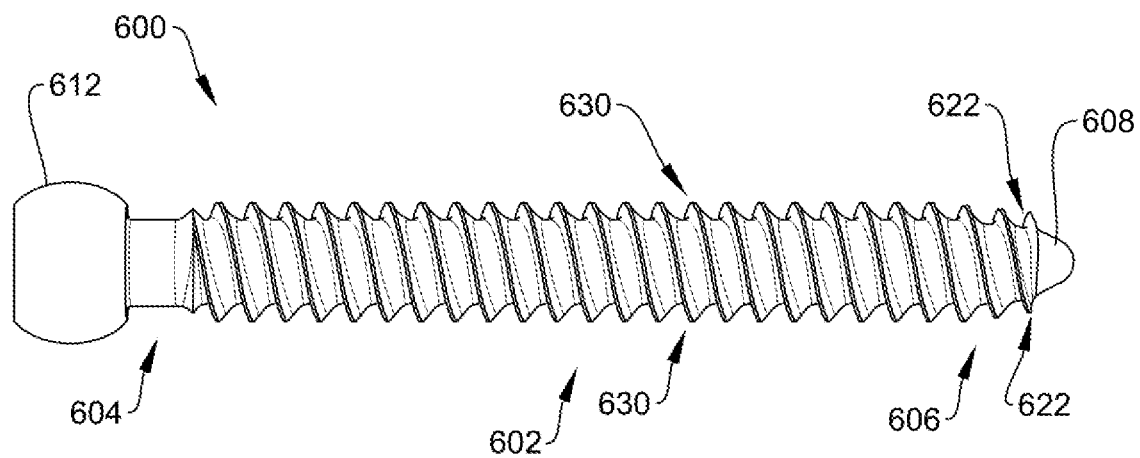
FIG. 5A is a side view of another embodiment of a bone screw.
Figure 5B:
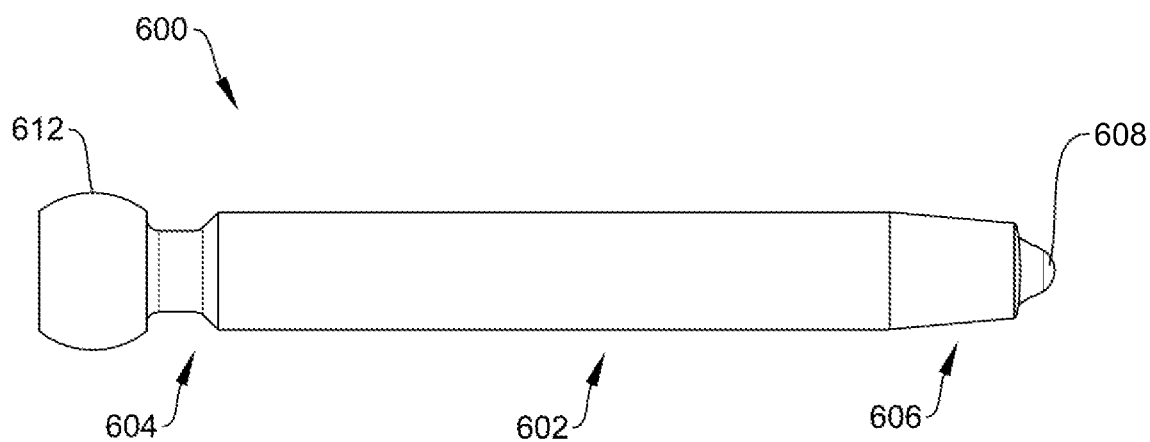
FIG. 5B is a side view of the shank of the bone screw of FIG. 5A, with the threads removed.
Figure 5C:
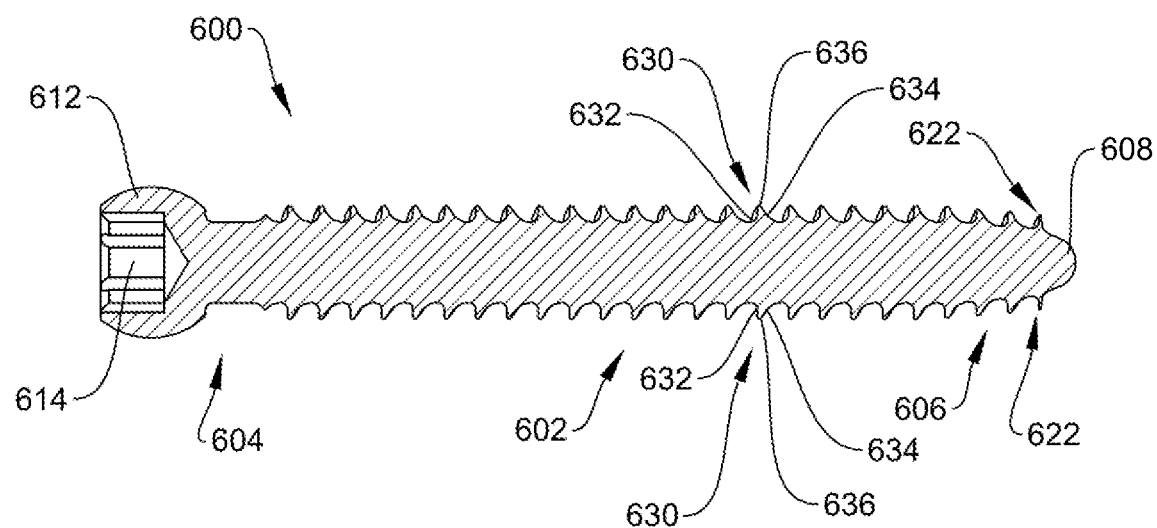
FIG. 5C is a cross-sectional side view of the bone screw of FIG. 5A.
Figure 5D:
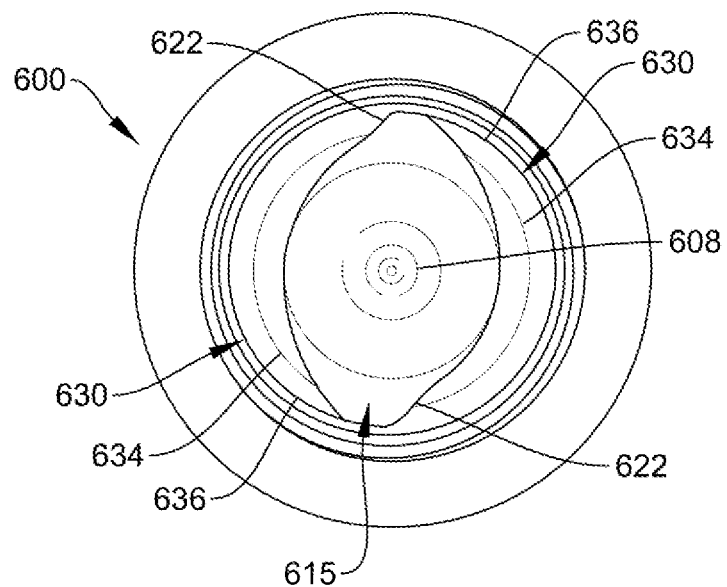
FIG. 5D is a distal-to-proximal end view of the bone screw of FIG. 5A.
Figure 5E:
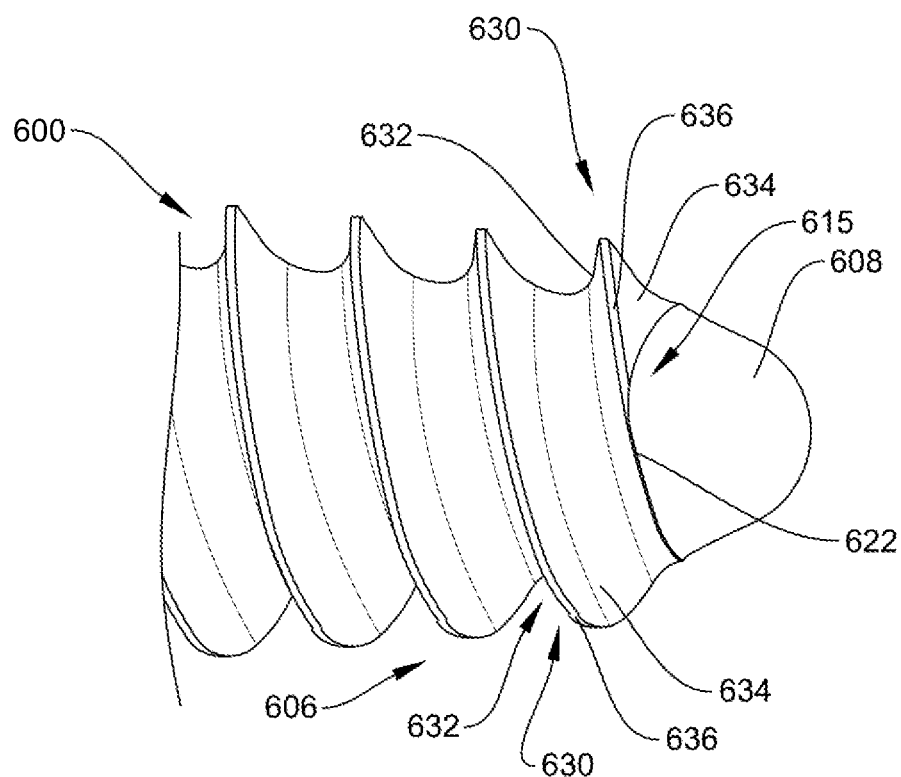
FIG. 5E is a perspective view of the distal tip of the bone screw of FIG. 5A.
Figure 5F:
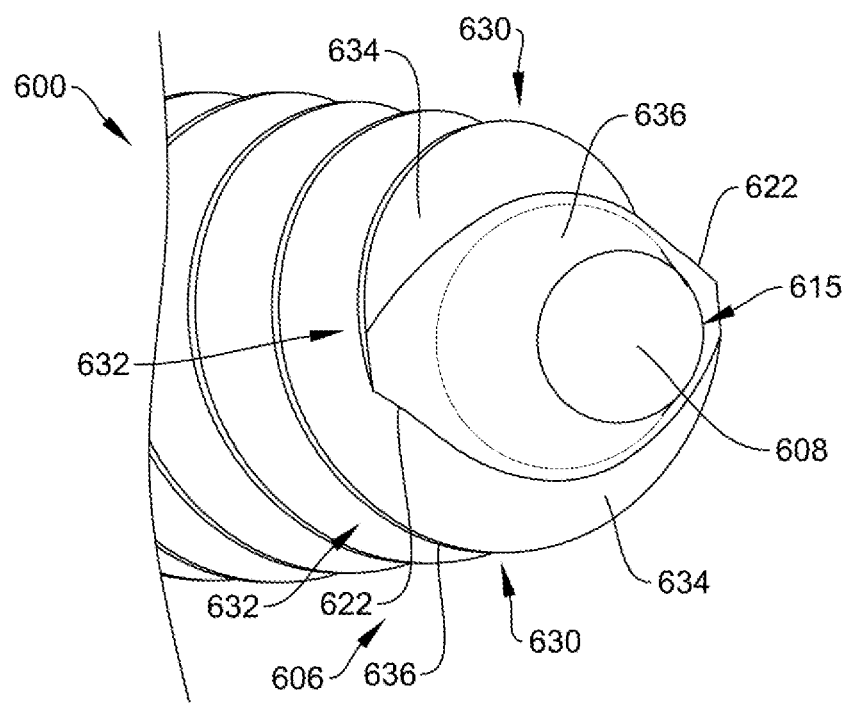
FIG. 5F is another perspective view of the distal tip of the bone screw of FIG. 5A.
Figure 5G:
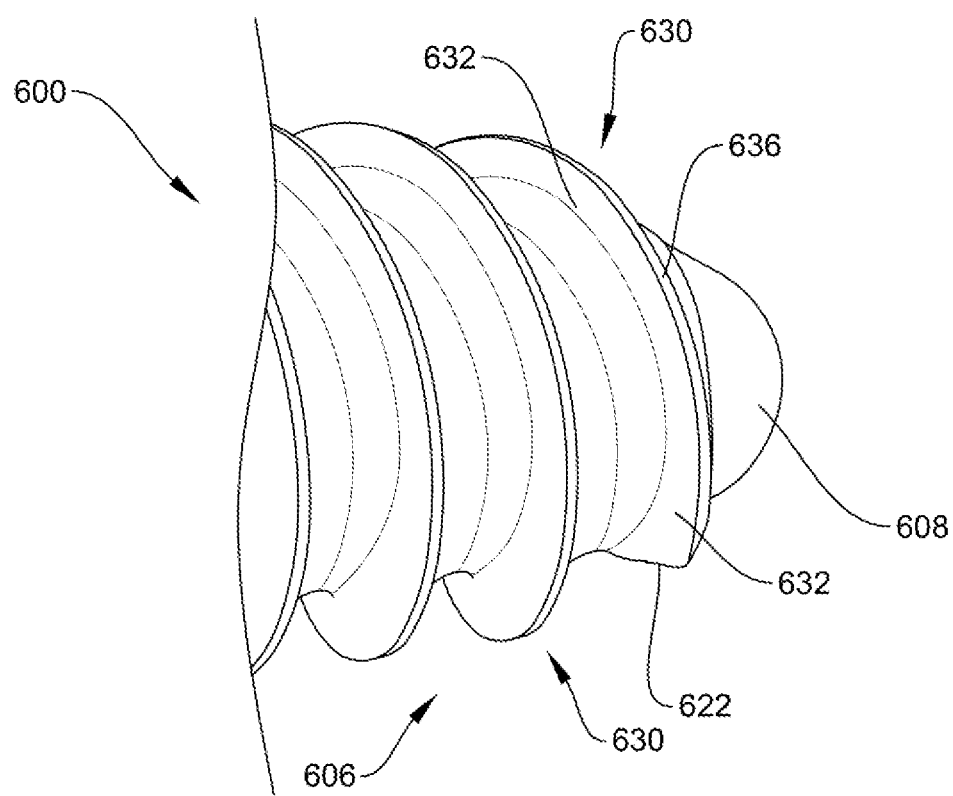
FIG. 5G is another perspective view of the distal tip of the bone screw of FIG. 5A.

Similar to the inner lumen 208 of the bone screw 200, an inner lumen can be formed in a bone screw with a concave distal end. For example, FIG. 4 illustrates a bone screw 400 similar to the bone screw 300 with an elongate shank 402 having a proximal end (not shown), a distal end 406, and a longitudinal axis L4. The illustrated screw 400 includes a head with a drive feature (not shown) configured to couple with a driver tool (not shown) for advancing the screw 400 into bone. The screw can have two or more threads 430 formed therealong that terminate at a distal tip on the distal end 406 with leading cutting edges 422 that are configured to cut bone. An inner lumen 408 can be formed through the elongate shank 402 along the axis L4, and the inner lumen 408 can be configured to receive a guidewire for facilitating placement of the bone screw in bone and/or bone cement to assist in anchoring the bone screw.

The distal facing surface in the bone screws disclosed herein can have various features formed thereon. For example, a leading nub or protrusion can be located on a distal end of a bone screw to allow a user to align the bone screw with a pilot hole formed in bone. For example, FIGS. 5A-5G illustrate a bone screw 600 similar to bone screw 100 with an elongate shank 602 having a proximal end 604 and a distal end 606. The screw 600 can also include a head 612 with a drive feature 614 configured to couple with a driver tool (not shown) for advancing the screw 600 into bone. The screw can have two or more threads 630 formed therealong. Each of the threads 630 can have a proximal surface 632, a distal surface 634, and an outer-most radial surface 636 that can extend at an angle to the proximal and distal surfaces 632, 634. The threads 630 can terminate at a distal tip on the distal end 606 with cutting edges 622 that are configured to cut bone. The distal tip configuration, including the cutting edges 622, can have the same configuration as the bone screws discussed above. However, in this embodiment, a nub 608 extends distally from a central or mid portion of a distal facing surface 615 of the bone screw 600. The nub 608 can have a variety of shapes, such as a generally conical shape. For example, the nub 608 can be cylindrical at a proximal base connecting to the distal facing surface 615 and can taper to a rounded or curved tip at a distal-most end. The nub 608 can be aligned with the central longitudinal axis and can be configured to fit into a pilot hole punched or drilled into bone to allow a user to quickly and easily line up the screw 600 with the bone, for example using the conical shape to ensure the screw 600 is securely positioned in the pilot hole. The diameter of the nub 608 is preferably smaller than the minor diameter of the threads 630 of the screw 600 to allow the cutting edges 622 to be formed and to help ensure that the threads 630 are large enough to still engage bone as the screw 600 is advanced into bone.

Figure 6:
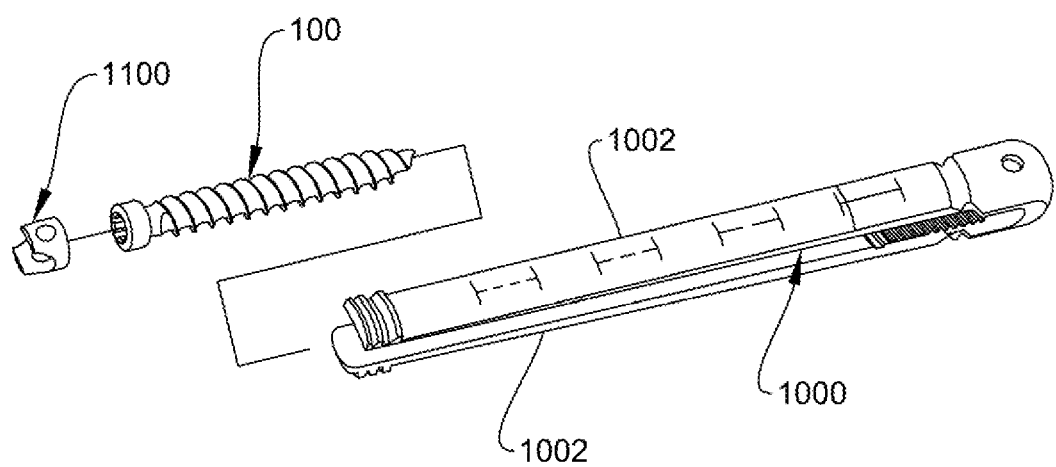
FIG. 6 is a perspective view of the bone screw of FIG. 1 shown with a receiver member and a compression cap to form a bone screw assembly.

In certain embodiments, the bone screws and shanks disclosed herein can be part of a bone anchor assembly. For example, as illustrated in FIG. 6, the bone screw 100 can be used with a polyaxial receiver 1000 and a compression cap 1100. The receiver 1000 can be in the form of a U-shaped body having screw extension tabs 1002 extending proximally therefrom. The receiver 1000 can have an inner cavity configured to seat the head 112 of the bone screw 100. The elongate shank 102 can extend through an opening in a distal end of the receiver 1000. The compression cap 1100 can be configured to be received in the receiver 1000 and positioned proximally from the bone screw 100. A spinal rod (not shown) can be positioned between the screw extension tabs 1002, and it can be seated in a proximal portion of the compression cap 1100. The assembly can also include a set screw (not shown) configured to be received between the screw extension tabs 1002, and it can apply a distal force to the spinal rod and the compression cap 1100 to lock the rod within the receiver 1000 and to lock the bone screw 100 in place relative to the receiver 1000. The outer surfaces of each of the screw extension tabs 1002 can include a feature, such as a recess, dimple, notch, projection, or the like, to facilitate connection of the receiver 1000 to instruments. For example, the screw extension tabs 1002 can include an arcuate groove at the respective free end of the tabs. Such grooves are described in more detail in U.S. Pat. No. 7,179,261, issued on Feb. 20, 2007, which is hereby incorporated by reference herein. Additionally, the bone screw 100 can be a favored angle screw, for example as disclosed in U.S. Pat. No. 6,974,460, issued on Dec. 13, 2005, and in U.S. Pat. No. 6,736,820, issued on May 18, 2004, both of which are hereby incorporated by reference herein. Alternatively, the bone anchor assembly can be a conventional (non-biased) polyaxial screw in which the bone screw pivots in the same amount in every direction. The surgical instruments disclosed herein can be configured to operate in conjunction with bone anchor assemblies of the type known in the art. Further information on screws can be found in U.S. patent application Ser. No. 13/648,184, filed on Oct. 9, 2012, which is hereby incorporated by reference herein. In some embodiments, a kit can be provided that includes one or more of the screws disclosed herein along with one or more screw assemblies, such as that illustrated in FIG. 8. For example, an exemplary kit can include a plurality of screws and/or screw assemblies of varying type and size, such that a surgeon can select the appropriate screw and/or screw assembly for a particular application.

In use, the bone screws 100, 200, 300, 400, 600 can be inserted into a body of a patient, either as part of a screw assembly or as part of another procedure. Using the bone screw 100 as an example, the distal end 106 of the bone screw 100 can be placed against bone, such as a vertebral pedicle, e.g., in the cervical spine of a patient. A driver tool (not shown) can engage the drive feature 114, and the driver tool can be rotated to rotate the bone screw 100, e.g., clockwise, relative to the bone. As the cutting edges 122 rotate, they can cut away bone and cause the screw 100 to advance forward into the bone. The threads 130 can engage bone, which can secure the bone screw 100 in bone. The driver tool can continue to be rotated until the bone screw 100 is fully driven into the bone. For example, a user can position at least two cutting edges 122 formed along an outer perimeter of the distal facing surface 115 of the bone screw 100 in contact with a bone surface in the cervical spine of a patient. The cutting edges 112 can engage the bone surface, and the cutting edges 122 can be defined by a portion of the outer perimeter of the distal facing surface 115 and the proximal surface 132 of at least two threads 130. Rotating the bone screw 100 can cause the cutting edges 112 to cut away bone to advance the bone screw into bone. The bone screw 100 can be positioned at an angle other than 90 degrees relative to the bone surface, and a distal protrusion on the distal facing surface 115 can be inserted into a guide hole formed in the bone. A central region of the distal facing surface 115 can be positioned proximal of the cutting edges 122 such that the central region does not contact the bone surface when the at least two cutting edges are positioned in contact with the bone surface.

The screws disclosed herein can be formed from any of a variety of materials. In some embodiments, the screws can be formed from non-absorbable materials, such as polysulfone, or metals such as titanium and titanium alloys. In other embodiments, the screws can be formed from or can include a coating made of a biocompatible, bioabsorbable material that can reduce immunological problems associated with having a foreign substance within the body over a prolonged period of time. Exemplary materials from which the screws disclosed herein can be formed include bioabsorbable elastomers, copolymer combinations such as polylactic acid-polyglycolic acid (PLA-PGA), and bioabsorbable polymers such as aliphatic polyesters, poly(amino acids), copoly (ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. In some embodiments, the screws can be formed from polylactic acid, or a composite blend of tricalcium phosphate and polylactic acid. One or more coatings can be used on the bone screws, for example coatings to promote bone growth or improve bone adherence to the bone screw. The screws disclosed herein can be formed from a single, unitary material and structure or can be formed from one or more materials listed above.

The screws disclosed herein can be provided in any of a variety of sizes, depending on patient anatomy, procedure type, screw assembly size, and various other parameters which will be readily apparent to one having ordinary skill in the art. In some embodiments, the screws disclosed herein can have a variety of lengths, for example, about 30 mm to 60 mm or about 80 mm to 100 mm, and can have a variety of diameters, such as about 3.0 mm, 3.5 mm, 4.0 mm, 4.5 mm, 5 mm, or 5.5 mm.

In the present disclosure, like-numbered components of the embodiments generally have similar features, and thus within a particular embodiment each feature of each like-numbered component is not necessarily fully elaborated upon. Sizes and shapes of the devices described herein, and the components thereof, can depend at least on the anatomy of the subject in which the devices will be used, the size and shape of components (e.g., spinal rods) with which the devices will be used, and the methods and procedures in which the devices will be used. The figures provided herein are not necessarily to scale. Although the devices and methods disclosed herein are generally directed to surgical techniques, they can also be used in applications outside of the surgical field. Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A bone screw, comprising:
    an elongate shank defining a central longitudinal axis, the elongate shank having a proximal end, a distal end with a conical distal tip region that tapers distally inward, and a distal facing surface; and
    at least two threads formed on the elongate shank, each thread terminating at the distal end in a leading cutting edge positioned radially outward of the central longitudinal axis and defined by an intersection between a proximal-facing surface of the thread and the distal facing surface of the conical distal tip region, the distal facing surface having an oblong shape with first and second curved edges extending along opposed sides thereof, the first and second curved edges each having a concave region and a convex region, and the distal facing surface having third and fourth convex edges extending along only a radially outermost perimeter of the distal facing surface relative to the central longitudinal axis.

2. The bone screw of claim 1, wherein the at least two threads comprise first and second threads that are offset from one another by 180 degrees.

3. The bone screw of claim 1, wherein the at least two threads are radially equidistant from each other around the elongate shank.

4. The bone screw of claim 1, wherein the leading cutting edge of each of the at least two threads extends along the concave region.

5. The bone screw of claim 1, wherein the convex regions are positioned circumferentially about the central longitudinal axis.

6. The bone screw of claim 1, further comprising a distal protrusion extending distally from the distal facing surface along the central longitudinal axis, the distal protrusion having a diameter that is less than a minor diameter of the elongate shank.

7. The bone screw of claim 1, wherein the distal facing surface has a conical shape and forms an acute angle with a plane extending perpendicular to the central longitudinal axis of the elongate shank.

8. The bone screw of claim 1, wherein the distal facing surface extends proximally from the at least two cutting edges such that the distal facing surface is concave.

9. The bone screw of claim 1, wherein the elongate shank is non-cannulated.

10. A bone screw, comprising:
    a non-cannulated elongate shank having a proximal end, a distal end, and a central longitudinal axis extending therebetween, the elongate shank having a major diameter along at least a proximal portion thereof, a conical distal tip region at the distal end that tapers distally inward, a distal facing surface having an edge defining an outer perimeter of the distal facing surface, the outer perimeter of the distal facing surface having an oblong shape with concave regions and convex regions, and the distal facing surface of the elongate shank being concave;
    at least two cutting edges formed along a portion of the outer perimeter of the distal facing surface; and
    at least two threads extending along the elongate shank, each thread having a proximal surface and a distal surface, and the proximal surface of each thread terminating at one of the at least two cutting edges.

11. The bone screw of claim 10, wherein the at least two cutting edges are positioned distally of a mid-point of the distal facing surface positioned on the central longitudinal axis.

12. The bone screw of claim 10, wherein the at least two threads comprise first and second threads that are offset from one another by 180 degrees.

13. The bone screw of claim 10, wherein at least a portion of the edge defining the outer perimeter of the distal facing surface is defined by an intersection between the distal facing surface and the distal surface of the at least two threads.

14. The bone screw of claim 10, further comprising a distal protrusion extending distally from the distal facing surface along the central longitudinal axis, the distal protrusion having a diameter that is less than a minor diameter of the elongate shank.

* * * * *